United States Patent [19]

Hasegawa et al.

[11] Patent Number: 5,376,795
[45] Date of Patent: Dec. 27, 1994

[54] EMISSION-TRANSMISSION IMAGING SYSTEM USING SINGLE ENERGY AND DUAL ENERGY TRANSMISSION AND RADIONUCLIDE EMISSION DATA

[75] Inventors: Bruce H. Hasegawa, South San Francisco; Robert G. Gould; Thomas F. Lang, both of San Francisco; J. Keenan Brown, San Jose; Joseph A. Heanue, Berkeley; Christopher E. Cann, San Francisco, all of Calif.

[73] Assignee: Regents of the University of California, Oakland, Calif.

[21] Appl. No.: 958,980

[22] Filed: Oct. 9, 1992

Related U.S. Application Data

[63] Continuation-in-part of Ser. No. 549,890, Jul. 9, 1990, Pat. No. 5,155,365.

[51] Int. Cl.⁵ ............................................. G01T 1/166
[52] U.S. Cl. ........................... 250/363.04; 364/413.24; 250/369
[58] Field of Search ............... 364/413.19, 413.21, 364/413.22, 413.24; 250/363.04, 369

[56] References Cited

U.S. PATENT DOCUMENTS

| 3,914,607 | 10/1975 | Cho et al. | 250/308 |
| 4,029,963 | 6/1977 | Alvarez et al. | 378/5 |
| 4,578,803 | 3/1986 | Macovski | 378/156 |
| 4,633,398 | 12/1986 | Gullberg et al. | 378/901 |
| 5,210,421 | 5/1993 | Gullberg et al. | 250/363.04 |

FOREIGN PATENT DOCUMENTS

| 92974 | 6/1983 | Japan | 250/363 |
| 1405819 | 6/1988 | U.S.S.R. | 378/4 |
| 9100048 | 1/1991 | WIPO | 250/363.04 |

OTHER PUBLICATIONS

J. S. Fleming, "A Technique for Using CT Images in Attenuation Correction and Quantification in SPECT," Nuclear Medicine Communications 10, pp. 83–97, 1989.
Park, "use of Simultaneous Transmission-Emission Scanning in the Diagnosis of Pericardial Effusion," J. Nucl. Med. (USA), 13 (6), Jun. 1972, pp. 347–348.
Peppler, "Combined Transmission-Emission Scanning Using Dual-Photon Absorptiometry," Ph.D. Thesis, Univ. Wisconsin, 1981.
Kuhl, "Transmission Scanning: A Useful Adjunct to Conventional Emission Scanning for Accurately Keying Isotope Deposition to Radiographic Anatomy," Transmission Scanning, vol. 87, pp. 278–284, Aug. 1966.
Briggs, "Combined Emission-Transmission Scanning of the Skeleton," Work in Progress, vol. 90, pp. 348–350, Feb. 1968.
Cohn, "A Whole-Body Counter with an Invariant Response to Radionuclide Distribution and Body Size," Phys. Med. Biol., 1969, vol. 14, No. 4, pp. 645–658.
Tothill, "Quantitative Profile Scanning for the Measurement of Organ Radioactivity," Phys. Med. Biol., 1971, vol. 16, No. 4, pp. 625–626.
Acts of 1972 Scientific Program: Technologists' Scien- (List continued on next page.)

Primary Examiner—Carolyn E. Fields
Attorney, Agent, or Firm—Townsend and Townsend Khourie and Crew

[57] ABSTRACT

Radionuclide emission imaging is improved by correcting emission-transmission data for attenuation along calculated path lengths and through calculated basis material. X-ray transmission data are used to develop an attenuation map through an object which is then used in reconstructing an image based on emission data. Radiation detection circuitry is provided which has different operating modes in detecting the x-ray and emission photons passing through the object. An iterative process is used to reconstruct the radionuclide distribution using the radionuclide projection data and the attenuation map based on physical characteristics of the object being imaged. Subsets of the complete radionuclide projection data are used to reconstruct image subsets of the radionuclide distribution. The image subsets can be generated concurrently with the acquisition of the radionuclide projection data or following acquisition of all data.

37 Claims, 9 Drawing Sheets

OTHER PUBLICATIONS tific Sessions Presented at 19th Annual SNM Meeting, Abstracts: Presented Orally, "Combined Transmission-Emission Scanning in Chest Disease," by Alfieri, vol. 13, No. 11, and Transmission Scanning as an Aid to the Interpretation of Routine Emission Scans, by Westerman, vol. 10, No. 6.

Suzuki, "Whole Body Transmission-Emission Scanning with Whole Body Camera," Whole Body Transmission-Emission Scanning, vol. 125, No. 4, pp. 978–980, Dec. 1975.

Nalcioglu, "Dual Energy Attenuation Correction for Single Photon Emission Computed Tomograph (SPECT)," IEEE Transactions on Nuclear Science, vol. NS-31, No. 1, Feb. 1984.

Bailey, "Improved SPECT Using Simultaneous Emission and Transmission Tomography," Jrnl. of Nuclear Med., vol. 28, No. 5, pp. 844–851, May 1987.

Murase, "A Comparative Study of Attenutation Correction Algorithms in Single Photon Emission Computed Tomography (SPECT)," Euro. Jrnl. of Nuclear Med., vol. 13, pp. 55–62, 1987.

SCAN Diagnostic Imaging, The Business Biweekly of Medical Imaging, vol. 2, No. 18, Sep. 28, 1988, pp. 7–8.

Levin, "Retrospective Geometric Correlation of MR, CT, and PET Images," Radiology, vol. 169, No. 3, pp. 817–823, 1988.

Thompson, "Simultaneous Transmission and Emission Scans in Positron Tomography," Presented at the IEEE Nuclear Science Symposium, Orlando, Fla., Nov. 9, 1988, Submitted to the IEEE Transactions on Nuclear Science, Feb. 1989.

Park, "Use of Simultaneous Transmission-Emission Scanning in the Diagnosis of Pericardial Effusion," Jrnl. of Nuclear Med., vol. 13, No. 6, pp. 347–348.

Product Literature-Imagine, 4 pages, M & SE Polyscan, Medical and Scientific Enterprises, Inc., Sudbury, Mass., undated.

Manglos, "Imaging of the Human Torso Using Cone-Beam Transmission CT Implemented on a Rotating Gamma Camera," Jrnl. of Nuclear Med., vol. 33, No. 1, Jan. 1992, pp. 150–156.

Stonestrom, "A Framework for Spectral Artifact Corrections in X-Ray CT," IEEE Trans. on Biomedical Engineering, vol. BME-28, No. 2 (ISSN 0018-9294), Feb. 1991, pp. 128–141.

Cann, "Precise Measurement of Vertebral Mineral Content Using Computed Tomography," Jrnl. of Computer Assisted Tomography, vol. 4, No. 4, pp. 493–500, Aug. 1980.

Tsui, "Correction of Nonuniform Attenuation in Cardiac SPECT Imaging," Jrnl. of Nuclear Med., vol. 30, No. 4, Apr. 1989, pp. 497–507.

Huizenga, "The Use of Computed Tomography Numbers in Dose Calculations for Radiation Therapy," Acta Radiologia Oncology 24 (1985) Fasc. 6, pp. 509–519.

EMISSION-TRANSMISSION IMAGING SYSTEM USING SINGLE ENERGY AND DUAL ENERGY TRANSMISSION AND RADIONUCLIDE EMISSION DATA

The Government has rights in this invention pursuant to Grant No. DK-39964 awarded by the National Institutes of Health.

BACKGROUND OF THE INVENTION

This is a continuation in part of copending application Ser. No. 07/549,890, filed Jul. 9, 1990, now U.S. Pat. No. 5,155,365 issued Oct. 13, 1992.

BACKGROUND OF THE INVENTION

This invention relates generally to x-ray transmission and radionuclide emission imaging systems. In a primary application the invention relates to a diagnostic imaging system where x-ray transmission data are used to derive material properties of the object imaged, which properties are then used directly to correct radionuclide emission data obtained from the same object using the same imaging system, herein referred to as X-SPECT.

Diagnostic imaging techniques can image both anatomical structure and physiological function of patients in whom the physician wishes to diagnose disease or follow treatment. In clinical settings, most of these diagnostic imaging techniques—including conventional film radiography, MRI, and CT—predominantly image structure rather than function. Unlike these anatomical imaging methodologies, in vivo measurement of tissue metabolism, perfusion, and biochemical processes is best performed with emission radionuclide-tracer techniques. In these techniques, a radionuclide or a compound labeled with a radionuclide is injected into a subject. The radiolabelled material concentrates in an organ or lesion of interest, and can show a concentration defect. At a prescribed time following injection, the pattern of concentration of the radiolabelled material is imaged by a rectilinear scanner, scintillation camera, single-photon emission computed tomography (SPECT) system, or positron emission tomography (PET) system. Applications of radionuclide imaging include quantitation of tissue metabolism and blood flow, evaluation of coronary artery disease, tumor and organ localization and volume determination, quantitation of receptor binding, measurement of brain perfusion, and liver imaging.

The radionuclide imaging procedure requires a means to define the path along which the emitted gamma-ray travels before striking the detector of the imaging system. The path can be a vector path, a line, narrow fan, or a narrow cone as defined by the detector or collimator. In rectilinear scanners, scintillation cameras, and SPECT systems, a collimator (typically made of lead or other high-atomic number material) is interposed between the object and the detector to define the gamma-ray path. In PET, the unique characteristics of positron annihilation radiation are coupled with electronic circuitry to define the vector path. In all cases, the only information obtained when a gamma-ray strikes the detector is the fact that the photon originated somewhere within the object along the vector path projected back from the detector. For projection imaging systems, a two-dimensional image is formed with the intensity of each picture element, or pixel, proportional to the number of photons striking the detector at that position. In SPECT or PET, the vector paths are determined for multiple projection positions, or views, of the object, and cross-sectional or tomographic images are reconstructed of the object using standard algorithms. Again, the intensity assigned to each vector path is proportional to the number of photons striking the detector originating along the path, and the intensity of each pixel in the reconstructed image is related to these vector path intensities obtained at multiple views.

In radionuclide imaging, it is desirable to obtain absolute values for radionuclide concentrations (or radionuclide uptake) at each point in the image. Attenuation of the emitted photons within the object, before they reach the detector, is a function of the energy of the photons and the exact composition of the material through which the photons pass to reach the detector. Photons emitted deeper within the object have a higher probability of attenuation than those emitted near the surface. In addition, the composition of the material (in terms of effective atomic number Z and electron density) affects the attenuation, with more attenuation if the path passes through high-Z or high-density regions. Thus, in order to calculate absolute uptake or concentration of a radionuclide in a region of an object, it is required that the path length of each type of material or tissue (or effective-Z and electron density path lengths) be known for each vector. Attenuation corrections for emitted photons are made from this knowledge, allowing accurate concentration values to be obtained.

The full clinical potential of radionuclide imaging has been seriously hindered by some important limitations. The spatial resolution and photon statistical limitations of radionuclide imaging frustrate accurate anatomical localization and hinder quantitation of the radionuclide distribution. Photon attenuation has been identified by the American Heart Association and leading nuclear cardiologists as a major deficiency in diagnosis of heart disease with SPECT, and is a major source of error in the measurement of tumor metabolism using radionuclide techniques. Quantitation is further complicated by the need for scatter compensation for imaging with both single-photon and positron-emitting radionuclides.

A number of researchers have shown that many of these limitations can be overcome through use of emission-transmission imaging techniques which combine anatomical (structural) information from transmission images with physiological (functional) information from radionuclide emission images. By correlating the emission and transmission images, the observer can more easily identify and delineate the location of radionuclide uptake. In addition, the quantitative accuracy of measurement of radionuclide uptake can be improved through use of iterative reconstruction methods which can account for these errors and improve the radionuclide images.

Currently existing medical imaging instrumentation has been designed for either emission or transmission imaging, but not both, and attempts to perform both compromise one or both of the data sets. In addition, as currently implemented, iterative reconstruction algorithms are too slow to converge and therefore impede the flow of information in a hospital setting. Virtually all clinical tomographic systems use analytic rather than iterative reconstruction algorithms which, unlike iterative reconstruction techniques, have the major advantage that the image reconstruction process can occur concurrently with the acquisition of the image data.

The efficiency of analytic approaches is compromised by their inability to account for the quantitative errors of photon attenuation, scatter radiation, and spatial resolution losses mentioned above.

The prior art in this field includes several different approaches to localize and quantify the uptake of radionuclides in the human body. One approach uses stereotactic techniques or computer processing methods to correlate functional information from SPECT or PET images with morphologic information from magnetic resonance imaging (MRI) or CT. This technique has the advantage that it can be applied retrospectively without acquiring new image data from the patient. However, these approaches are computationally intensive, require that the patient be scanned separately on two systems, and have only been successful in the head where the skull limits motion of internal anatomical structures.

A second set of prior art describes instrumentation used to detect emission and transmission data using instruments with single or multiple detectors. Several investigators have acquired both the emission and transmission images, with a radionuclide point, line, or sheet used as the transmission source which is placed on the opposite side of the body from the scintillation camera. This approach has been applied more recently using SPECT. Studies have shown that this technique is capable of producing adequate attenuation maps for attenuation correction to improve quantitation of radionuclide uptake, and that some modest anatomical localization of the radionuclide distribution is also possible.

An alternative approach uses specially-designed instruments for emission-transmission imaging. For example, Kaplan (International Patent Application No. PCT/US90/03722) describes an emission-transmission system in which the emission and transmission data are acquired with the same detector (single or multiple heads). An alternative emission-transmission imaging system (disclosed in SU-1405-819-A) uses x-ray transmission data and two detectors for determining the direction of the photons to improve detection efficiency. However, an exact method of correcting emission data based on transmission data is not described by either Kaplan or in SU-1405-819-A.

Other prior art notes that the map of attenuation coefficients required for the attenuation correction procedure can be obtained from a separate x-ray transmission CT scan of the patient, although a specific method of generating an attenuation map at the photon energy of the radionuclide source is not known. Specific techniques to determine the attenuation map of the patient from single-energy transmission measurement using radionuclide or x-ray sources have been described which are limited to sources emitting monoenergetic (line) spectra rather than broad spectra such as those typically obtained from an x-ray source.

Specific algorithms for correcting beam-hardening artifacts use single-energy x-ray data and dual-energy x-ray data. As used herein, the term "single-energy x-ray" describes methods in which an image is generated by integrating the x-ray signal over a single range of photon energies. As used herein, the term "dual-energy x-ray" describes methods in which two images are generated by integrating the signal over two different photon energy ranges. Thus, either "single-energy x-ray" or "dual-energy x-ray" includes methods in which the x-ray source emits an x-ray beam having either a narrow of broad spectrum of energies. Algorithms for correcting beam-hardening artifacts by using basis-material measurements derived from single-energy or dual-energy x-ray data have been presented but without describing how these measurements can be applied to correction of radionuclide data. Especially for single-energy measurements, the correction techniques associated therewith are principally directed at the removal of beam-hardening streaks and nonuniformities which disturb the qualitative evaluation of images produced with CT.

A key element has been the combination of the emission and transmission data in a reconstruction algorithm which corrects the radionuclide distribution for photon attenuation. Several authors have described analytic algorithms such as filtered backprojection in which the radionuclide data is modified using an attenuation map to correct for attenuation errors. Among their advantages, these analytic algorithms are fast and require only a single step to reconstruct the radionuclide distribution. However, they are inexact and utilize a uniform attenuation map in which the value of the attenuation coefficient is assumed to be constant across the patient. Other reconstruction algorithms are iterative and use an exact attenuation map and the radionuclide projection data to estimate the radionuclide distribution across the patient. Maximum likelihood estimation is one statistical method that can be used for image reconstruction. A maximum likelihood estimator appropriate for radionuclide tomography based on an iterative expectation maximization algorithm (ML-EM) has been described. The ML-EM algorithm is easy to implement, accounts for the Poisson nature of the photon counting process inherent with radionuclide imaging, and it produces better images than filtered backprojection. In addition, ML-EM algorithms can incorporate physical phenomena associated with radionuclide tomography, such as photon attenuation and scatter, detection efficiency, and geometric aspects of the imaging process. Iterative weighted least squares/conjugate gradient (WLS/CG) methods have also been proposed and used for radionuclide tomography. Overall, WLS/CG reconstruction algorithms converge faster than ML-EM procedures, while still incorporating the statistical nature of radionuclide imaging, and permit compensation for photon attenuation and scatter, detection efficiency and geometric response. Iterative algorithms have been successfully used for both SPECT and PET imaging.

The major disadvantage of iterative algorithms is their computational burden. Iterative algorithms are iterative procedures and are started with an initial image estimate that either corresponds to a constant radionuclide density throughout the image plane to be reconstructed or corresponds to constant density throughout the highly sampled "reconstruction circle" and zero outside this region. This estimate is unlikely to be representative of the actual distribution of radionuclide in a patient, and a large fraction of the total iterations required to generate useful images may be necessary to reveal the real qualitative structure of the radionuclide distribution. Thus, these algorithms often require 30 to 50 iterations to yield visually acceptable images, and possibly several hundred iterations to generate quantitatively accurate reconstructions.

It also is possible to use filtered backprojection to produce initial image estimates for iterative reconstruction algorithms. Filtered backprojection algorithms can operate concurrently with the emission data acquisition, and they are the method currently used for most clinical radionuclide imaging systems due to their efficiency and ability to produce useful images. Unfortunately it is generally not possible to modify filtered backprojection algorithms to accurately account for details of the collimator geometry, or for the effects of scatter, especially in regions where there are large inhomogeneities in these properties, or details of the collimator geometry. Therefore, this approach can speed up iterative techniques slightly, although the improvement in convergence speed has not been dramatic. Thus, many investigators have pursued various methods of speeding the convergence of ML-EM algorithms or reducing the time required per iteration. Methods include exploiting the symmetry of the imaging system, multigrid approaches, high frequency enhanced filtered iterative reconstruction, expectation maximization search (EMS) algorithms, rescaled gradient procedures, vector-extrapolated maximum likelihood algorithms, and hybrid maximum likelihood/weighted least squares (ML/WLS) algorithms. However, all iterative reconstruction methods require significantly more computer time than filtered backprojection algorithms to generate useful images. The iterative ML-EM and WLS/CG algorithms mentioned above assume complete sets of radionuclide projection data exists prior to commencement of the reconstruction procedure. The requirement to acquire complete sets of projection data is especially important in radionuclide system because clinical emission imaging systems typically require several minutes to acquire projection data, making iterative reconstruction techniques impractical.

SUMMARY OF THE INVENTION

The present invention is a system for acquiring correlated transmission and emission images with a dedicated imaging instrument, and includes the algorithms to process the emission and transmission data to calculate the radionuclide concentrations in the anatomical regions being imaged. A radiation detector is provided to record radionuclide images like a standard radionuclide imaging system. In addition, the system contains a transmission source and detector for acquisition of transmission images from which the anatomy of the body can be determined. The transmission source may be either a radionuclide or an x-ray tube or other radiation generating device. The transmission detector may be the same detector or a different detector from the radionuclide detector. In addition, a method is provided to maintain the relative spatial locations between the emission and transmission data sets. This can be performed by placing a localizing apparatus on the patient which is scanned concurrently with the patient. Alternatively, because the emission and transmission detectors are supported on a common gantry or embodied in a single detector, it is possible to perform calibration scans on a phantom prior to acquisition of the patients from which the emission and transmission data can be registered. As defined herein, the concept of single imaging system includes those embodiments in which the emission and transmission detectors are mounted on separate but adjacent gantries which share a common patient table. This will allow the patient to be translated from one imaging system to the other without having the patient move relative to the patient-support of the common table.

Both the emission detector and the transmission detector are electronically connected to data acquisition electronics which receive the detector signals and generate signals representative of the radiation striking the detector. Typically, the detector signals are digitized and stored in a computer as projection data showing the emission and transmission radiation signals recorded from the patient. From the transmission data, the computer uses a tomographic reconstruction algorithm to calculate an attenuation map which shows the distribution of attenuation coefficients at each point across the volume imaged in the patient.

Because the emission and transmission data are registered spatially, the attenuation map can be used as input data which is used in the reconstruction of the radionuclide data. In this process, the attenuation map is used to correct the radionuclide projection for absorption by overlying tissue and is necessary for quantitative accurate calculations of the radionuclide concentrations within the patient. Typically, this is performed with an iterative reconstruction algorithm which also can correct for other physical perturbations such as photon-statistical noise, scattered radiation, and partial-volume effects. The transmission image also can be used as a priori information in Bayesian reconstruction algorithms to improve anatomical definition in the radionuclide image.

For visual evaluation, color-mapped radionuclide emission data can be superimposed on high-resolution transmission image in order to correlate physiological information with structural information. The system allows the operator to define a region-of-interest on a correlated transmission image which has better statistics and spatial resolution than the radionuclide image. Thus, the inherent features of the emission-transmission system can improve the localization, accuracy, and precision of in vivo radionuclide measurements used to assess a patient's physiological status. Potential applications of emission-transmission imaging include tumor and organ localization and volume determination, myocardial perfusion, quantitation of receptor binding, measurement of brain perfusion, and liver imaging.

The invention and objects and features thereof will be more readily apparent from the following detailed description of illustrative embodiments and appended claims when taken with the drawings.

BRIEF DESCRIPTION OF THE DRAWINGS

Like elements in the Figures have the same reference numerals.

DETAILED DESCRIPTION OF ILLUSTRATIVE EMBODIMENT

Figure 1A:
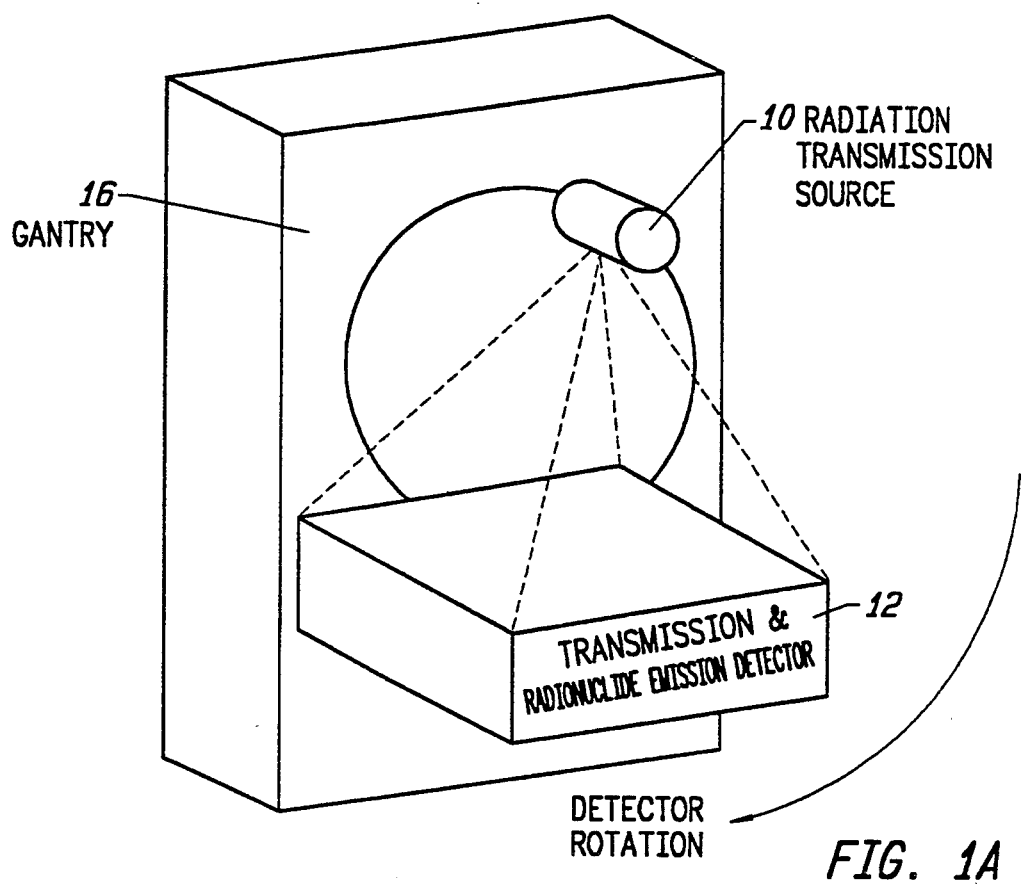
FIGS. 1A, 1B, 1C, and 1D are isometric views of hardware of a system in accordance with four embodiments of the invention.
Figure 1B:
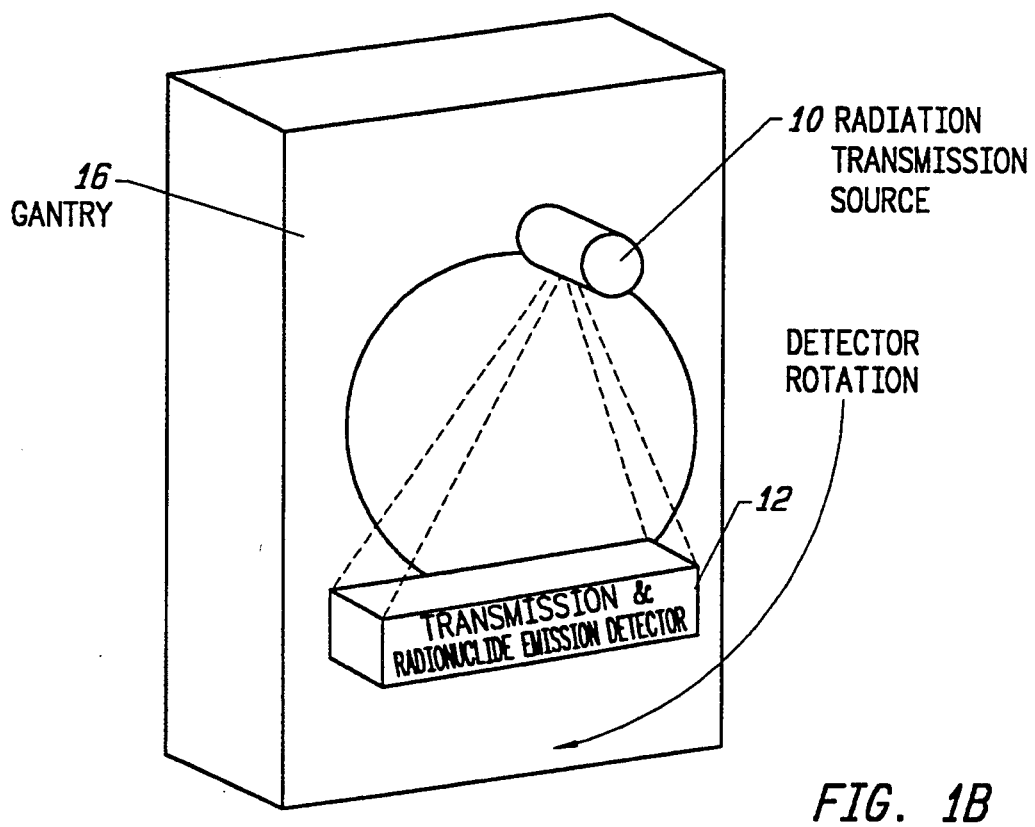

FIGS. 1A and 1B are isometric views of two embodiments of the emission-transmission imaging system in accordance with the invention showing a radiation source 10, a combined transmission detector, and a radionuclide emission detector 12 all mounted to a gantry 16.

Figure 2:
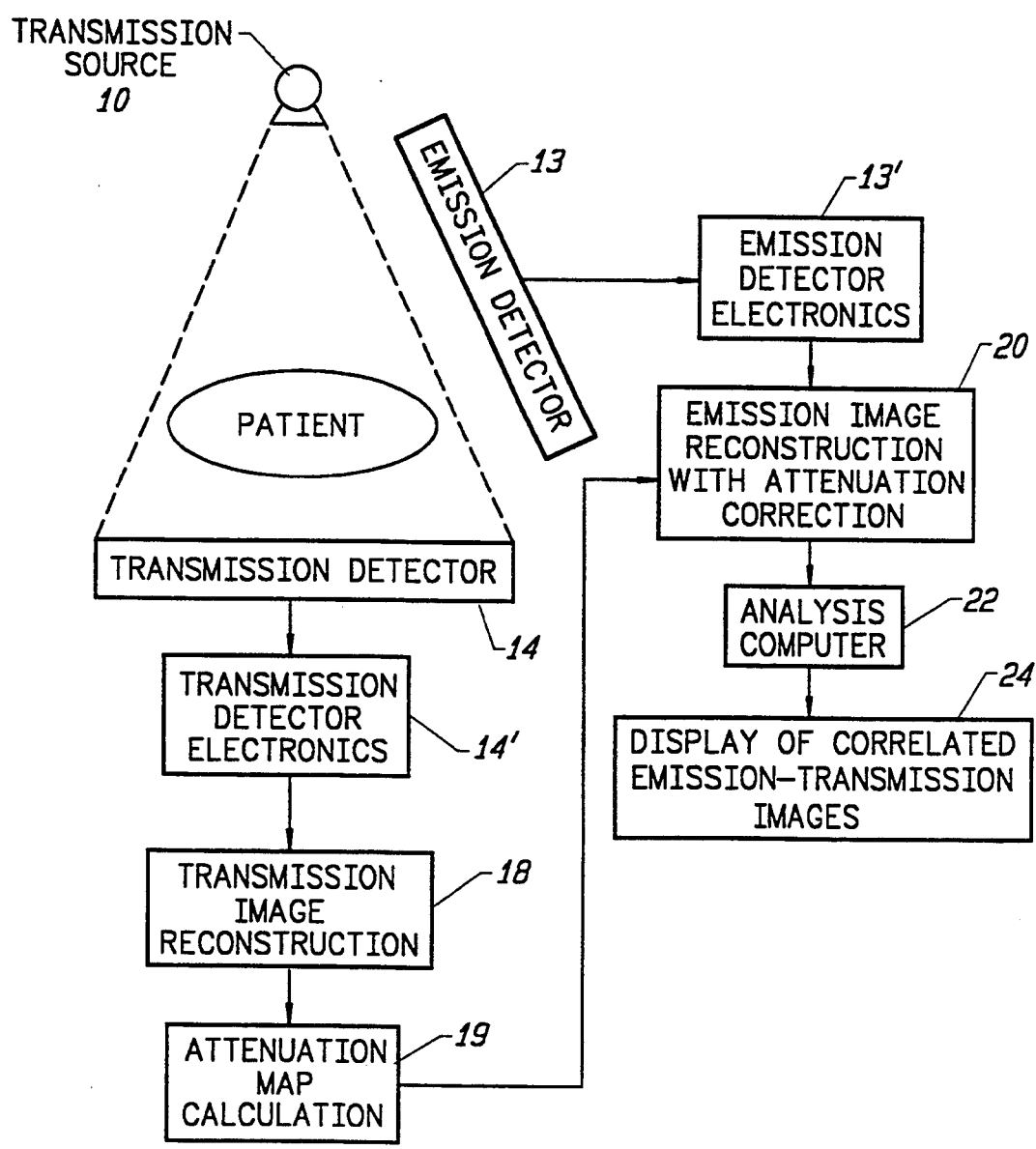
FIG. 2 is a flow diagram illustrating signal processing in the system of FIG. 1.

FIG. 2 illustrates the detection and processing of signals. Both the emission detector 13 and transmission detector 14 are electronically connected to data acquisition electronics 13', 14' with the transmission data used to generate an attenuation mad which is then used to correct the emission data. In accordance at 18 with a feature of the invention, the emission image can be reconstructed at using concurrent iterative reconstruction algorithms with attenuation correction from the attenuation map at 19. Computer analysis is provided at 22, and image display is provided at 24.

Figure 1C:
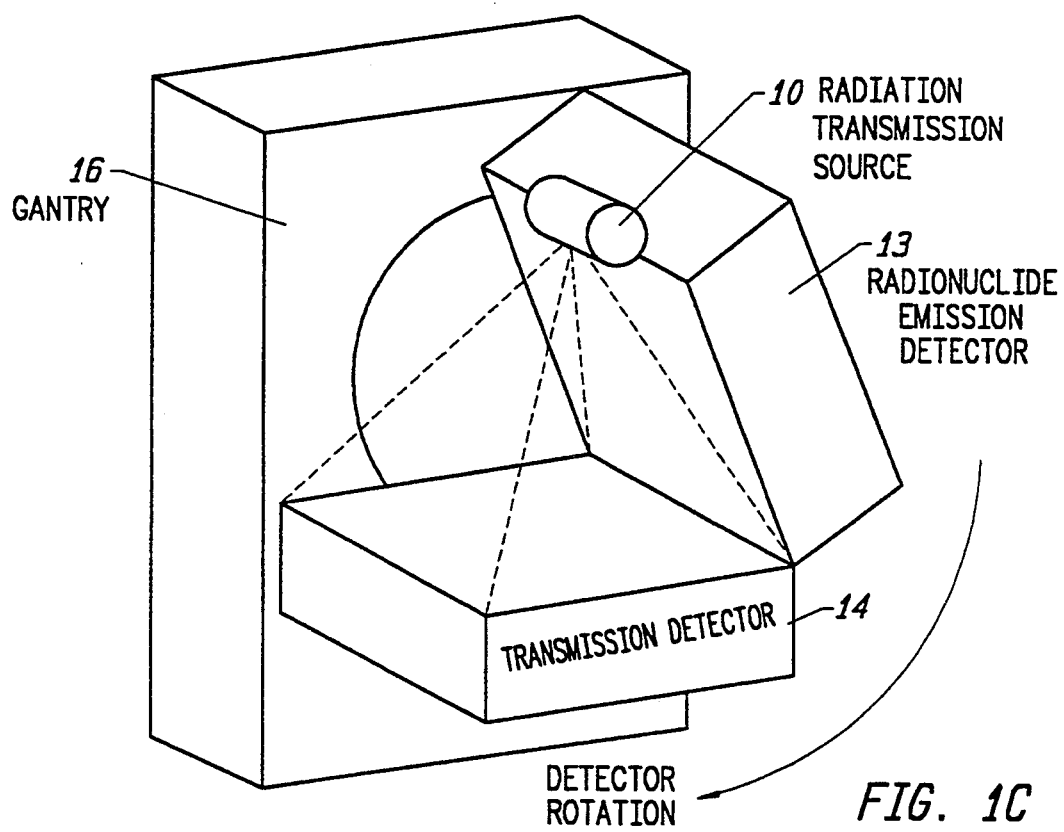
Figure 1D:
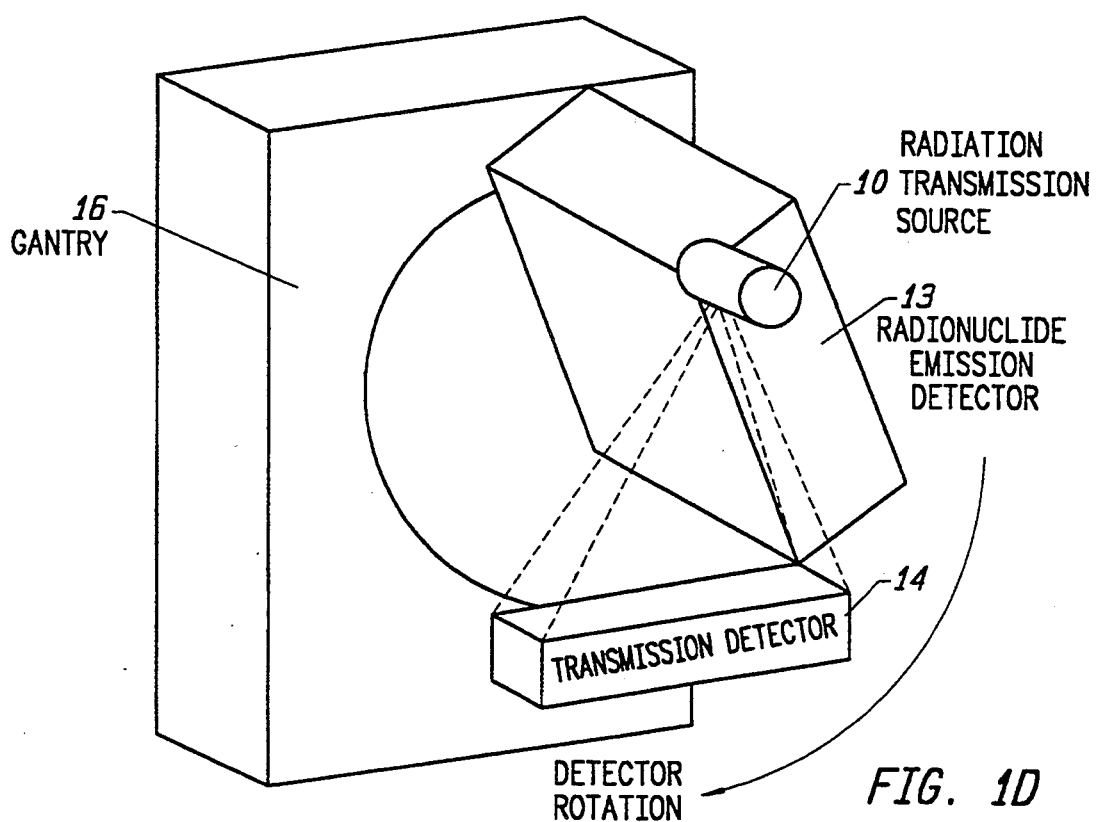

The system requires detectors for both the emission and transmission data A single detector array can be used for both emission and transmission imaging, as shown in FIGS. 1A and 1B. An alternative approach shown in FIGS. 1C and 1D uses separate detector arrays 13, 14 for emission and transmission imaging, respectively. In FIG. 1A a two-dimensional transmission detector is used, while in FIG. 1B a one-dimensional transmission detector array is used.

One-dimensional detectors acquire images of a single plane in the patient during a single tomographic scan, while two-dimensional detector arrays acquire images from an entire volume. However, the transmission detector can be designed to use a limited cone-beam or fan-beam geometry. For example, single-slice and spiral fan-beam geometries can be used while translating the object across the stationary x-ray fan-beam. These approaches have the disadvantage that a longer period of time is required to obtain the x-ray data, but have the advantages that this detector configuration are less expensive and have better scatter-rejection characteristics.

Conventional CT scanners typically use scintillation detectors coupled to photodiodes, which are operated in a current mode. Radionuclide imaging systems use scintillators such as sodium iodide or bismuth germinate (BGO) which are coupled to photomultiplier tubes or photodiodes. However, other detector technologies can be used for emission-transmission imaging. In the pulse-counting regime, semiconductor detectors can be used, including HPGe, cadmium telluride, zinc cadmium telluride, and mercuric iodide. Scintillation detectors also can be operated in a pulse-counting mode, but are impractical for x-ray transmission measurements due to their low count-rate capabilities. Similarly, multiwire proportional counters operate in a pulse-counting mode, but have inadequate count-rate capabilities and poor detection efficiencies for the x-ray energies used in the emission-transmission system. Among current-integrating systems, pressurized xenon ionization detectors have been used for x-ray CT but are difficult to manufacture and to operate as area detectors. Hydrogenated amorphous silicon (a-Si:H) plates are being investigated as two-dimensional radiation detectors which integrate the photodiode, capacitor, and FET switch on a single substrate. Image intensifiers are compatible with cone-beam x-ray geometries, but suffer from pin-cushion distortion and veiling glare which complicate quantitative measurements. In addition, they are relatively large, heavy, and expensive, especially in formats large enough for body scanning with a cone-beam geometry.

Scatter radiation contributes a significant error to quantitative transmission measurements in CT, and these errors are aggravated in a system using an area detector. Therefore, it is desirable but not essential that the transmission detector is operated with a collimator to reject scatter. In addition, scatter compensation algorithms can be applied to the transmission projection data before it is reconstructed using a tomographic algorithm. Radionuclide imaging devices typically are operated with energy discrimination which reduces the amount of scatter radiation in the recorded data. In addition, several scatter compensation algorithms have been developed to provide additional corrections for scattered radiation. In emission-transmission imaging, the radionuclide detector can receive large amounts of scattered radiation during acquisition of the x-ray transmission image. To avoid this source of error from affecting the radionuclide data, the emission and transmission projection data can be acquired sequentially rather than simultaneously. During acquisition of the x-ray transmission data by the transmission detector, the scintillation camera can be protected from turning these high photon fluxes using a lead-lined cover. Alternatively, the scintillation detector used for radionuclide imaging can be turned off during the transmission scan to protect the photomultiplier tubes from damage from the high photon fluxes. Scintillation detectors used for radionuclide imaging commonly are operated with photomultiplier tubes (PMT's), which can be damaged by high photon fluxes.

Compensating filters can be used to decrease dynamic range, and thereby improve both the scatter and signal-to-noise characteristics of the recorded transmission signal. Compensating filters also introduce spatially-dependent changes in x-ray beam-hardening, which can introduce errors into quantitative transmission measurements. As will be described herein below, accuracy errors contributed by beam-hardening artifacts are corrected using uniformity corrections as well as iterative correction techniques. Additional corrections are derived from the use of aggressive filtration of the x-ray beam to derive quasi-monoenergetic spectra. It also is possible to use dual-energy CT to derive attenuation maps of sufficient accuracy and precision for attenuation-correction of the radionuclide data.

Aggressive x-ray beam filtration also can be used to reduce errors in the x-ray transmission measurement which results from use of iodinated contrast media which have attenuation coefficients with a k-edge within the photon energy range used to acquire the transmission data. This nonlinearity introduces errors into calculation of the attenuation map from the beam-hardening correction described in this disclosure and can require that we can filter the x-ray beam so that its spectrum falls above the iodine k-edge to avoid these nonlinearities.

Figure 3A:
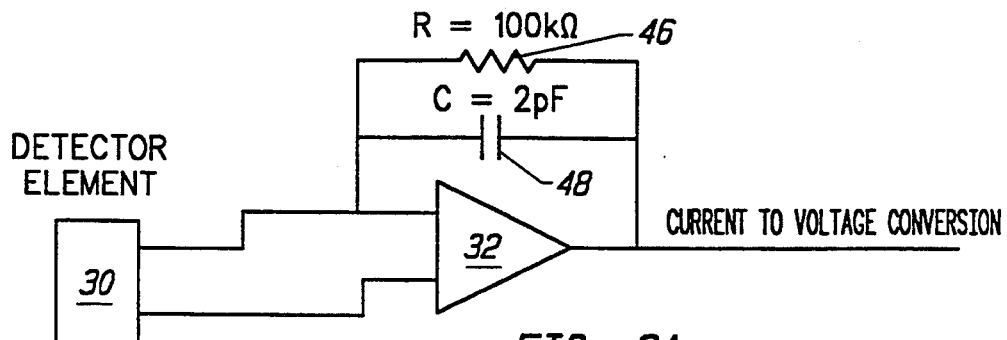
FIGS. 3A–3C are schematics of detectors in the system of FIG. 1.
Figure 3B:
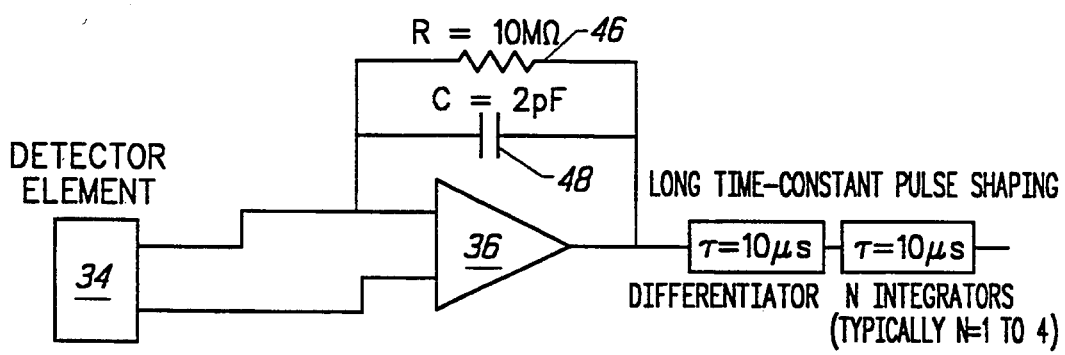
Figure 3C:
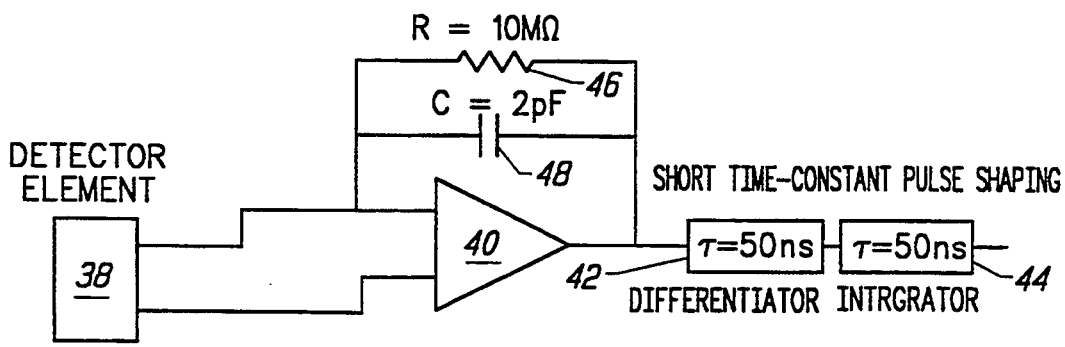

As noted above, the emission-transmission system can use either separate detectors or a single detector to record the emission and transmission data. The ideal implementation of this instrument is to use a single detector so that emission and transmission data can be spatially registered, and potentially can be recorded simultaneously. However, the use of a single detector is complicated because differences in the acquisition requirements of the transmission and emission data are extreme. The transmission data are acquired with a point or line source, typically at high data rates, and do not require energy discrimination. Therefore, transmission CT scanners use detectors operated in the "current" or "integrating" mode, where the electronic circuitry including integrating amplifier 32 attached to the detector element 30 reads the current produced by absorption of one more photons in a unit of time (FIG. 3A). In comparison, radionuclide imaging typically is performed at low data rates and requires energy discrimination so that unscattered emission photons can be separated from those which are scattered within the body. Emission imaging devices therefore use a detector 34 and integrator 36 operated in the "pulse" or "counting" mode in which signals are generated for single photons and where the signal amplitude is proportional to the photon energy (FIG. 3B). Finally, when simultaneous emission-transmission imaging is performed, the circuitry including detector 38, integrator 40, differentiator 42, and integrator 44 must operate at high count rates (to accommodate the photon flux from the transmission source) but must operate in a "count" or "pulse" mode to allow discrimination of the emission and transmission photons, as well as discrimination of scattered and unscattered photons from the emission source (FIG. 3C). For example, the component values in FIG. 3 are chosen to illustrate these applications for a high-purity germanium detector element having a thickness of 6-mm and a surface area of 2-mm × 10-mm and with a charge collection time of 50 ns. In FIG. 3A, the feedback resistor 96 and capacitor 48 values are chosen to produce the largest usable signal from the amplifier which is compatible with the photon flux received and the charge-conversion characteristics of the detector. In FIG. 3B and FIG. 3C, the values of the feedback resistor 46 and capacitor 48 are selected to provide a time constant which is long in comparison to the charge-collection time of the detector. However, in FIG. 3B, the pulse-shaping time constants and number of integrators are chosen to maximize the signal-to-noise characteristics of the circuit which optimizes the energy resolution capabilities for photon-counting at low count rates. In comparison, in FIG. 3C, the pulse-shaping time constants are chosen to be consistent with the charge collection time of the detector to maximize count rate with moderate energy resolution.

Figure 4:
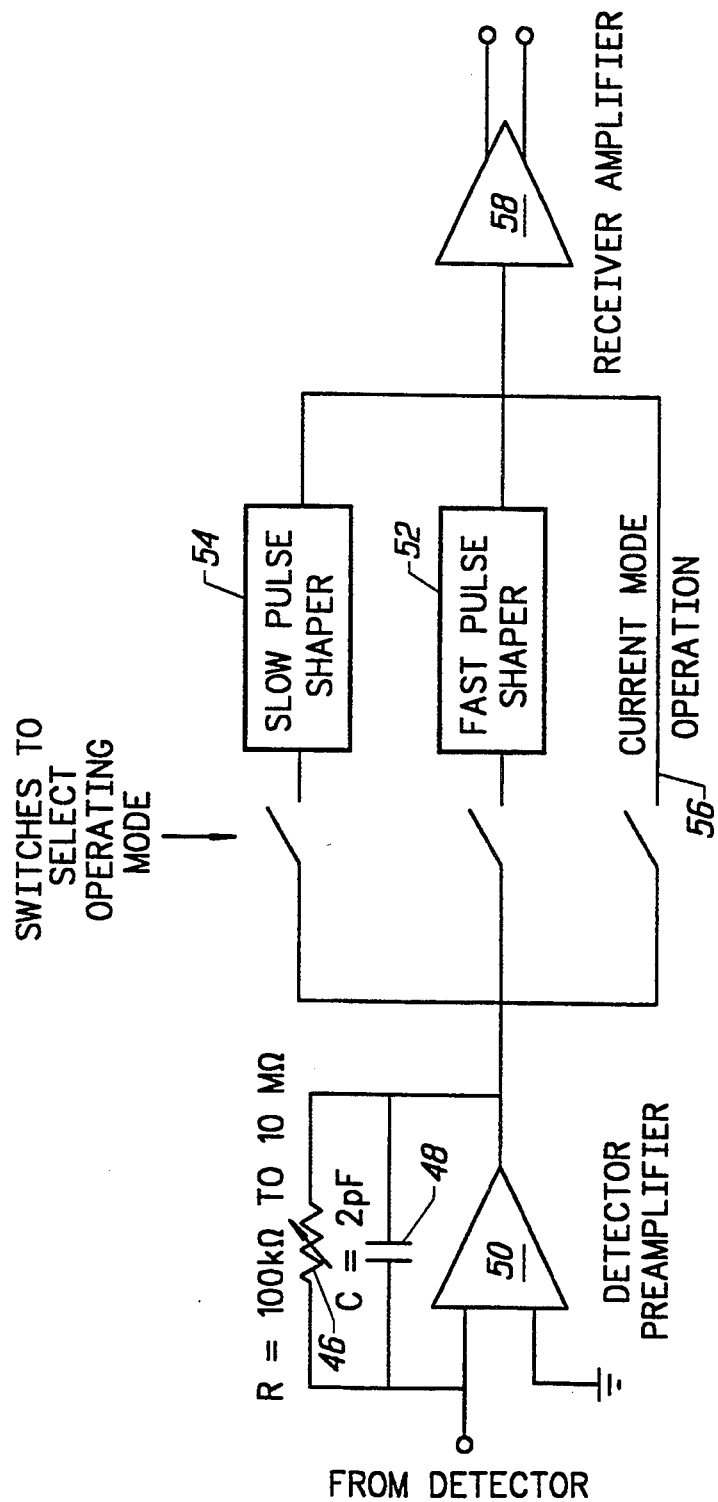
FIG. 4 is a schematic of a triple mode detector circuit for use in the system of FIG. 1.

One possible implementation involves a novel "triple-mode" electronic circuit for the detector readout shown in FIG. 4. The input amplifier 50 can function in either charge-sensitive pulse mode or in current mode. This flexibility is achieved by using a variable feedback resistor 46 which can be made larger for charge sensitive operation or smaller for current mode operation. In addition, the feedback capacitance 48 is chosen such that it is suitable as an integrating capacitor for pulse-mode operation or as a compensating capacitor for current mode operation. Following the input amplifier 50 and before the receiver amplifier, several pulse shaping stages are available in parallel; the desired stage can be switched in for a given application. Fast pulse shaping is available at 52 for high count rate applications (x-ray imaging), and slow pulse shaping is at 54 available for low count rates (radionuclide imaging). No pulse shaping is necessary in current mode at 56. In brief, the triple mode electronics allow the detector to be read out in current mode, fast pulse mode, and slow pulse mode. The circuit can be assembled from discrete components, or can be fabricated as an application-specific integrated circuit in which the resistor is implemented by a MOSFET operated in the ohmic region.

As previously noted, the prior art has suggested that x-ray CT can be used to obtain attenuation maps but has not described specific procedures to do so. This procedure is complicated by x-ray beam hardening that introduces errors in the quantitation of attenuation coefficients obtained with this technique. These errors can be compensated by conventional beam-hardening correction algorithms that use a CT scan of a uniformity phantom having an appropriate diameter to normalize the CT scans of other objects. These uniformity correction coefficients are parameterized in a look-up table giving the normalization factor as a function of the diameter and distance from the rotational center of the object. This technique corrects "global" uniformity errors, but does not correct "local" beam-hardening errors between two heterogeneities (e.g., bones) in the reconstruction volume. Therefore, the imaging system in accordance with the invention uses techniques to correct beam-hardening errors contributed by soft-tissue, water, and bone within the scanned object.

Figure 5:
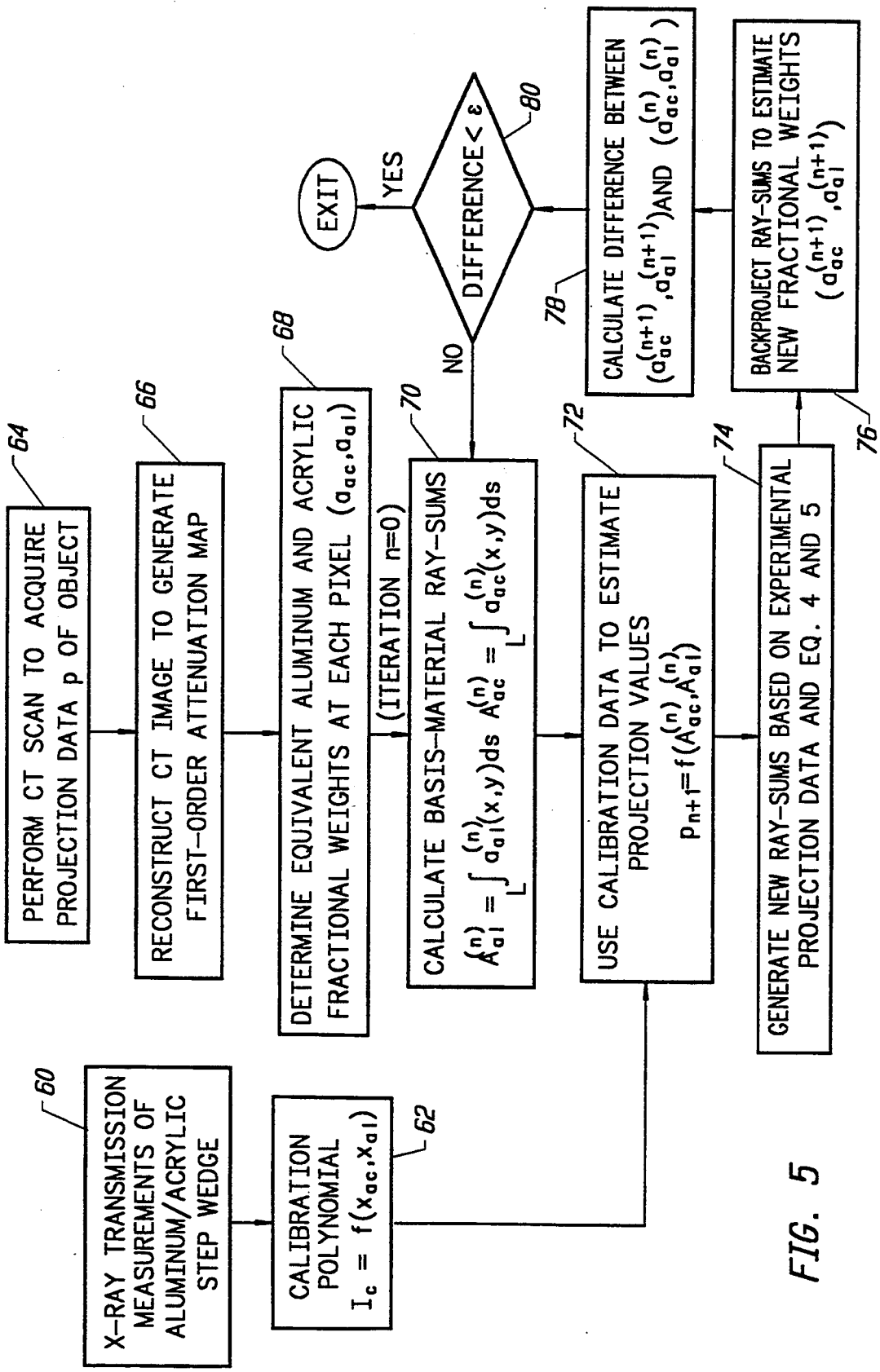
FIG. 5 is a flow chart of a beam-hardening correction algorithm in accordance with the invention.

A flow chart of one technique for calculating the attenuation map for x-ray measurements is shown in FIG. 5. The correction procedure uses calibration scan of a bidirectional step-wedge at 60 containing known thicknesses of aluminum and acrylic. The transmission data are approximated at 62 as $$I_c = f(A_{ac}, A_{al}) \tag{1}$$

where the measured calibration intensities $I_c$ are represented as a function (e.g., polynomial) of the known material thicknesses ($A_{ac}, A_{al}$) in the calibration phantom.

We then acquire at 64 projection data p of the object (i.e., phantom or patient), from which we reconstruct a tomogram at 66 using filtered backprojection or other standard technique. We assume voxels with more attenuation than acrylic contain a homogeneous mixture of acrylic and aluminum, while those with less attenuation than acrylic contain a homogeneous mixture of acrylic and air. Based on the reconstructed attenuation coefficients, we assign a fractional contribution of acrylic ($a_{ac}$) and aluminum ($a_{al}$) to each voxel in the tomogram at 68. (Because the attenuation properties of soft-tissue and bone can be approximated as linear combinations of acrylic and aluminum, each voxel could be equivalently expressed in terms of fractional weights of soft-tissue and bone.) The fractional weights are used as first estimates in the following iterative process to correct their values for beam-hardening.

In the iterative process, the $n^{th}$ estimate of the basis set coefficients ($a_{ac}^{(n)}, a_{al}^{(n)}$) are projected at 72 to give the $n^{th}$ estimate of the equivalent ray-sums ($A_{ac}^{(n)}, A_{al}^{(n)}$) of the two basis materials at 70

$$A_{ac}^{(n)} = \int_L a_{ac}^{(n)}(x,y)ds \quad \text{and} \quad A_{al}^{(n)} = \int_L a_{al}^{(n)}(x,y)ds \tag{2}$$

for each set of projection data. These values are used to obtain the $n^{th}$ estimate the projected transmission values $P_n$ from Eq. 1, so that $$p_n = f(A_{ac}^{(n)}, A_{al}^{(n)}) \tag{3}$$

Assuming the difference between $p_n$ and the experimental projection data p is small, error estimates ($\Delta_{ac}^{(n)}, \Delta_{al}^{(n)}$) for the ray-sums, ($A_{ac}^{(n)}, A_{al}^{(n)}$) can be determined from a first-order Taylor's series expansion of Eq. 1

$$p \approx f(A_{ac}^{(n)}, A_{al}^{(n)}) + \frac{\partial f}{\partial A_{ac}}\bigg|_{(A_{ac}^{(n)}, A_{al}^{(n)})} \Delta_{ac}^{(n)} + \frac{\partial f}{\partial A_{al}}\bigg|_{(A_{ac}^{(n)}, A_{al}^{(n)})} \Delta_{al}^{(n)} \quad (4)$$

and a second arbitrary constraint, such as $$\frac{\Delta_{al}^{(n)}}{\Delta_{ac}^{(n)}} = \frac{A_{al}^{(n)}}{A_{ac}^{(n)}} \quad (5)$$

Corrected estimates of the $n^a$ iterative ray-sums, $(A_{ac}^{(n)} + \Delta_{ac}^{(n)}, A_{al}^{(n)} + \Delta_{al}^{(n)})$ are determined at 74 for each experimentally measured projection, and the set back-projected at 76 to give the $(n+1)^{th}$ iterative estimate of the acrylic and aluminum densities for each voxel. This procedure is repeated until the acrylic and aluminum densities within each voxel are stable to within 0.5% (or other accuracy level) of the densities obtained on the previous iteration as determined at 78 and 80.

This iterative beam-hardening algorithm converges toward a pair of images describing the equivalent density contributions of the aluminum and acrylic basis materials for each voxel of the original uncorrected image. These values can be used to estimate the monoenergetic attenuation map used for attenuation correction of the radionuclide image. The attenuation map at the point (x,y) is calculated as $$\mu(x,y;E) = a_{ac}(x,y)\mu_{ac}(E) + a_{al}(x,y)\mu_{al}(E) \quad (6)$$

where E is chosen to be the photon energy of the radionuclide (e.g., 140 keV for $^{99m}$Tc, and where $\mu_{ac}(E)$ and $\mu_{al}(E)$ are the linear attenuation coefficients of acrylic and aluminum at the energy E. The resulting attenuation map then can be used as input data for the reconstruction of the radionuclide image. These data also can be analyzed directly for quantitative measurement of tissue components at each point in the image.

Figure 6A:
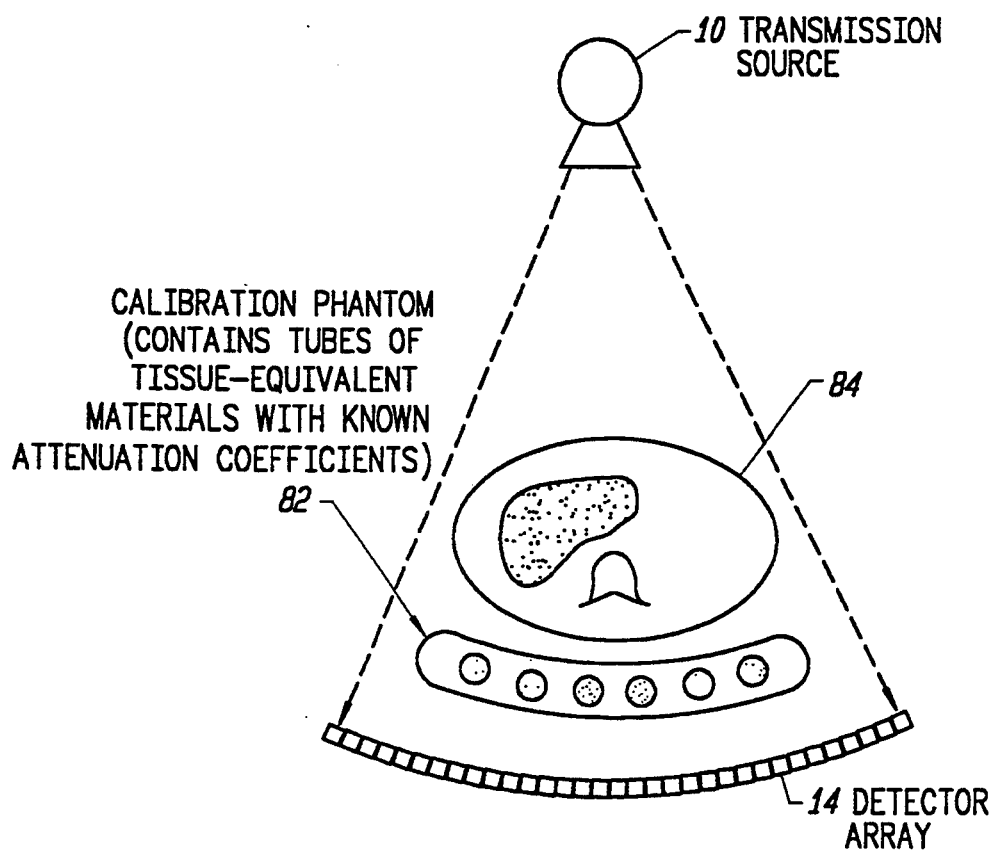
FIG. 6A illustrates a CT method of obtaining an attenuation map using a calibration phantom.
Figure 6B:
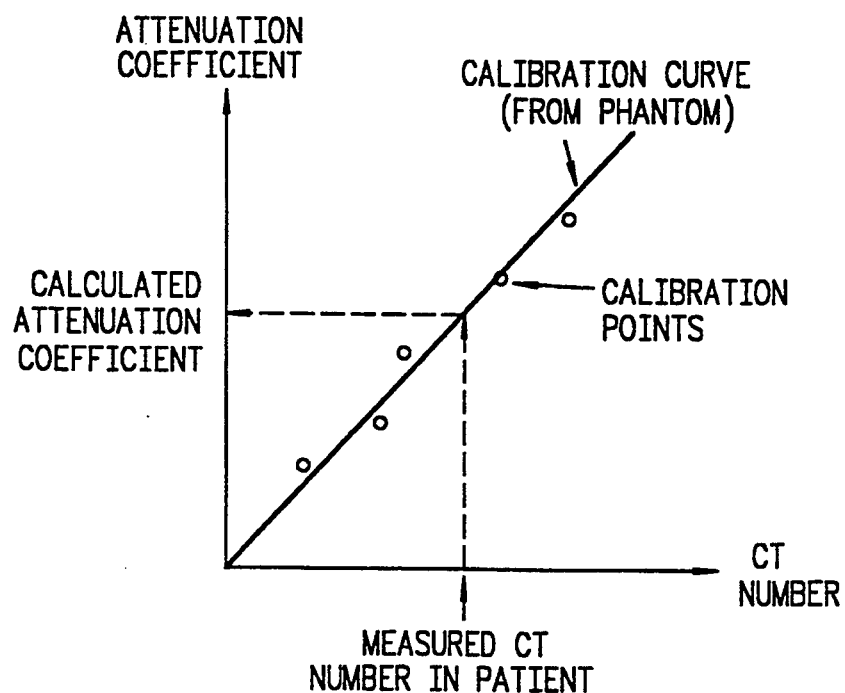
FIG. 6B illustrates the correlation between CT numbers and attenuation coefficients for known material properties.

Other techniques can be used to obtain an accurate attenuation map for this application. One class of these techniques uses a calibration phantom 82 which is scanned simultaneously rather than separately from the patient 84 as illustrated in FIG. 6A and 6B. The phantom includes distinct regions which contain materials similar in the x-ray attenuation properties to those found in the human body. After the patient and phantom are scanned, the image is read into a computer where the derived CT number from the various regions of the calibration phantom are related to their known material properties. The known material properties then can be correlated with the attenuation coefficients of these materials at the radionuclide energy, thereby giving an equation which transforms the measured CT numbers from the image to desired attenuation coefficients. In some cases, this relationship will be sufficient to generate the desired attenuation map. However, the existence of beam-hardening and other errors require that the calibration measurements be used to calculate material properties of the patient which are entered into an iterative correction algorithm such as that described above, which is used to generate an accurate attenuation map of the patient including corrections for beam-hardening errors.

In accordance with another feature of the invention, a new class of concurrent iterative reconstruction algorithms is provided. These "concurrent" algorithms reconstruct the image during (rather than after) acquisition of the radionuclide data, thereby speeding up the overall image reconstruction process. As with iterative reconstruction methods, the major motivation for using concurrent reconstruction algorithms is to account for physical effects so that qualitatively improved and quantitatively accurate images can be obtained. However, the concurrent iterative reconstruction algorithms process partial sets of projection data during the acquisition phase to dramatically reduce the elapsed time required to obtain and reconstruct the radionuclide image.

Two general approaches have been developed, which use only subsets of projections and which can be described in terms of the ML-EM algorithm as follows. From a numerical analysis perspective, the image reconstruction problem reduces to finding the global minimum (or maximum) of an "objective function" or "cost function." The objective function is constructed such that the image associated with the least (or greatest) cost is in some probabilistic sense "most" representative of the distribution of radionuclide within a patient. For ML-EM reconstruction algorithms, the goal of the reconstruction procedure can be stated as maximizing the following objective function:

$$O_{ML} = \sum_{d=1}^{N_d} \left[ \sum_{b=1}^{N_b} \lambda_n(b) w(b,d) + D^*(d)\log\left(\sum_{b=1}^{N_b} \lambda_n(b) w(b,d)\right) \right] \quad (7)$$

In the above equation, $\lambda$ is the $n^{th}$ iterative estimate of the radionuclide distribution, $D^*$ is the vector of measured counts for each detector in the imaging system, and the transition matrix w gives the probability of a photon emitted from pixel b being detected in detector d. The sum over d in Eq. 7 extends over all $N_d$ detectors in the acquired radionuclide data, while the sum over b extends over all $N_b$ pixels in the reconstructed radionuclide image. Physical aspects of the imaging process, including geometric response of the imaging system, and photon attenuation and scatter, are incorporated in the transition matrix, which includes information derived from the transmission image. The objective function for WLS/CG reconstruction algorithms is somewhat different, although the general goal of minimizing an objective function is identical to that of the ML-EM algorithm given in Eq. 7.

Figure 7A:
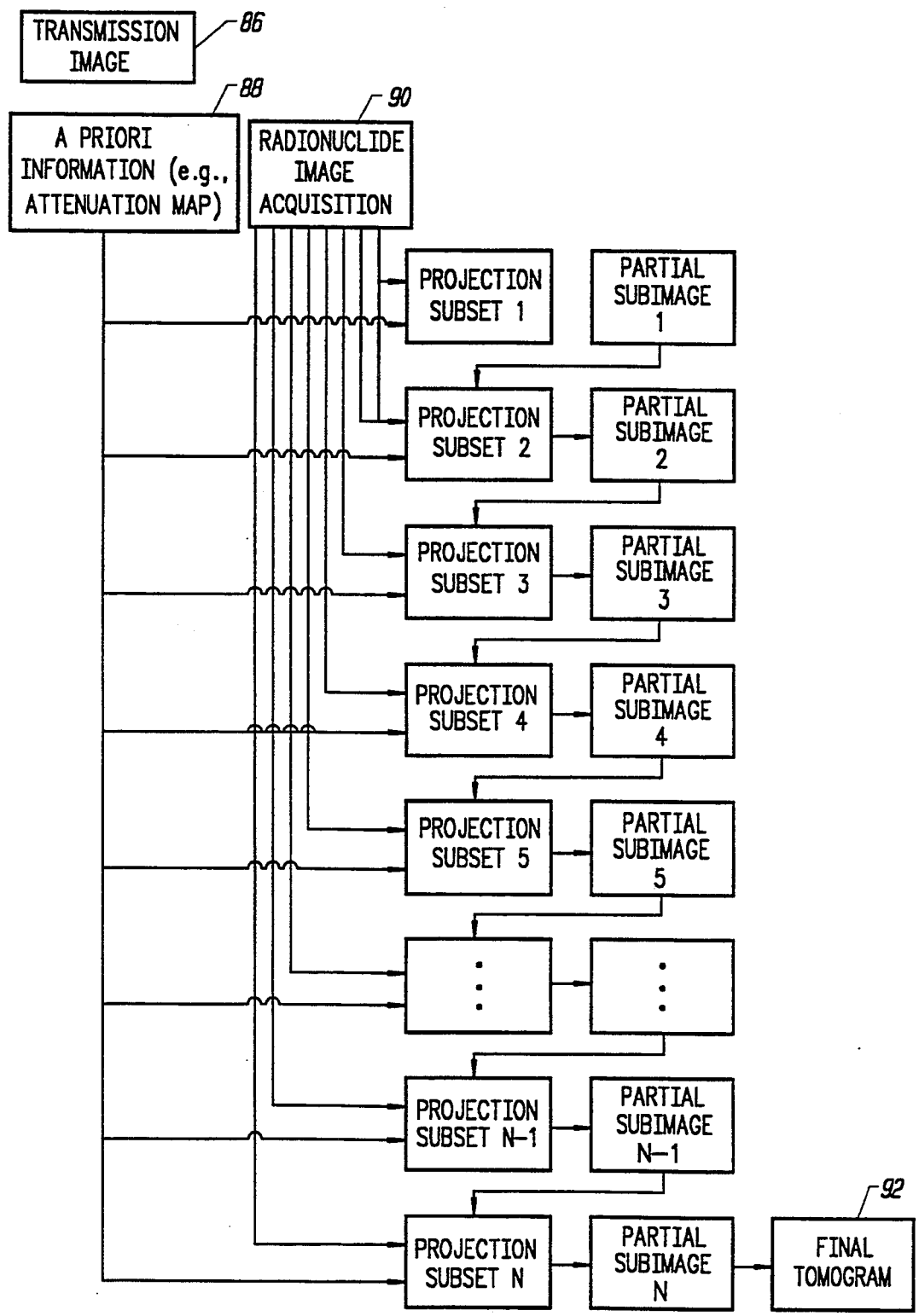
FIGS. 7A and 7B are flow diagrams illustrating two methods of concurrent iterative reconstruction in accordance with the invention.

The objective functions for the concurrent algorithms have the same form as Eq. 7, however, the sum over detectors, d, does not include all $N_d$ projections that are ultimately used to form the final image. This is a necessary requirement for these reconstruction methods to take place simultaneously with the acquisition of radionuclide projection data. For example, two approaches can be used to obtain the iterative image estimates, but differ in the manner used to generate subsets of projection data. The first approach for processing projection subsets, illustrated in FIG. 7A and referred to here as the method of "sequential subsets," will be started with a uniform image estimate at 86, 88 and some minimum number of projections, $N_{Min}$, available during the radionuclide scan at 90. Thus, the sum over detectors in the appropriate objective function contains $N_{Min}$ terms. A WLS/CG or ML-EM type algorithm will then be used to generate the first iterative image estimate. After the first iteration is completed, any new projections available from the radionuclide imaging system will be incorporated in the projection subset, and the next iterative image estimate will be generated. This method of sequentially adding projections to the reconstruction subset is continued until all $N_d$ projections are included in the reconstruction procedure. Additional iterations are performed with the complete set of projections until appropriate stopping conditions are satisfied for the final tomogram at 92.

Figure 7B:
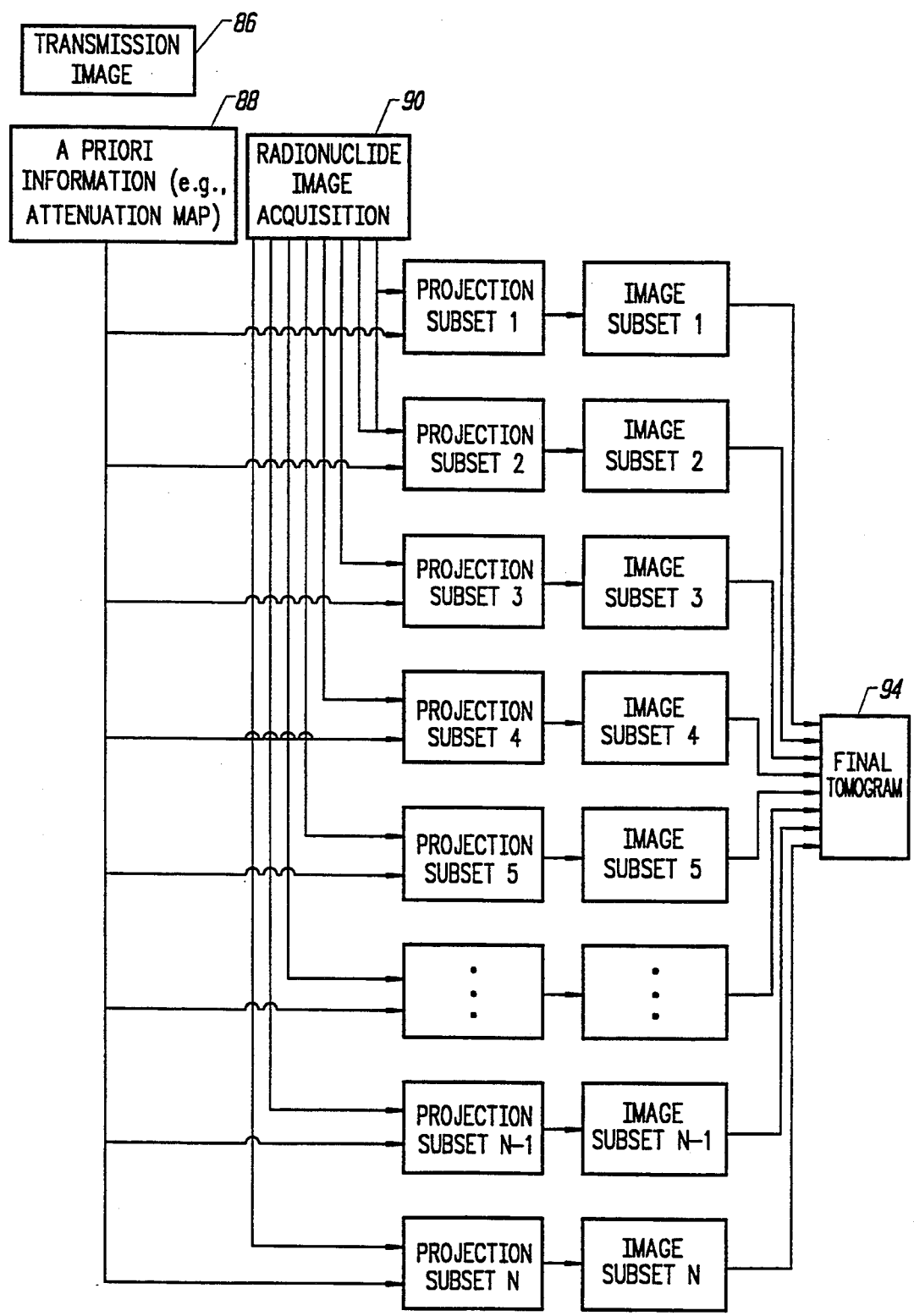

The second method for processing the radionuclide projection data, illustrated in FIG. 7B and referred to here as the method of "independent subsets," again starts with a 15 uniform image estimate and some minimum number of projections. A fixed number of iterations, $N_{iter}$, of a WLS/CG or ML-EM type algorithm is used to generate a "subimage" from this subset of projections. The next set of $N_{Min}$ projections available from the radionuclide imaging system will then be reconstructed in a similar manner. This procedure is repeated until subimages have been generated for all $N_d$ projections with each subimage reconstructed from $N_{Min}$ projections, and in general each projection appears in one and only one subset. In addition, it is reasonable that $N_{iter}$ should be chosen such that reconstruction of a subimage is completed just as the next subset of projections is available. The subimages are then combined at 94 to form an initial image estimate for the post acquisition iterative reconstruction routine with the following procedure. Each pixel in the combined image will be constructed from a weighted linear combination of pixels in the respective subsets. The weights are determined from the transition matrix w appearing in Eq. 7. First, let $p_i(b)$ be the probability that photons emitted from pixel b are detected in subset i. For example, this probability can be calculated as $$p_i(b) = \sum_{d_i} w(b, d_i) \quad (8)$$

where the sum over $d_i$ includes all projections in subset i. Pixel b in the iterative initial image estimate, $\lambda_0$, then may be described by $$\lambda_0(b) = \frac{\sum_{i=1}^{N_i} p_i(b)\lambda_i(b)}{\sum_{i=1}^{N_s} p_i(b)} \quad (9)$$

where i is indexed over all $N_s$ subimages, $\lambda_i$.

Although the concurrent image estimates will be of sufficient quality to be of limited clinical utility, generally additional processing is necessary. Therefore, the concurrent images will be used as initial image estimates with complete sets of projection data in conventional iterative reconstruction procedure. The concurrent image estimates will not be restricted to use the same underlying reconstruction method as is used in the post-acquisition reconstruction phase.

It has been assumed that angular views with the radionuclide imaging system are taken at consecutive angles, and projection subsets for the concurrent algorithms contain consecutive angular views. This is the logical sequence for acquiring data with a single detector array. However, the imaging system can have two or three radionuclide detector arrays, providing projections corresponding to vastly different angular views of the patient simultaneously. This reduces the total scan time, and will improve the convergence rate of concurrent algorithms when projection subsets are constructed from data with significantly varying angles. In the preceding discussion, we have described how these concurrent techniques can be applied to the tomographic reconstruction of radionuclide images. However, as used herein, the terms "concurrent iterative reconstruction" and "concurrent reconstruction" include those applications in which iterative reconstruction algorithms include a priori information in the reconstruction of either emission or transmission data. In the case of emission imaging, the a priori information can include an attenuation map, information about scattered radiation, corrections for partial-volume effects derived from the transmission image. In the case of emission or transmission imaging, the a priori information can include a description of spatial resolution loss due to the geometrical characteristics of the system or the collimator.

Thus, while the invention has been described with reference to illustrative embodiments, the description is illustrative of the invention and is not to be construed as limiting the invention. Various modifications and applications may occur to those skilled in the art without departing from the true spirit and scope of the invention as defined by the appended claims.

What is claimed is:

1. An emission-transmission imaging system comprising
   a) a radiation source for emitting a photon spectrum,
   b) detector means for selectively detecting photons corresponding to said photon spectrum and photons corresponding to radionuclide emission,
   c) means for positioning said radiation source facing said detector means with an object positionable therebetween, said object having a radionuclide therein,
   d) data acquisition means connected with said detector means for receiving transmission signals from said detector means representative of the photon spectrum photons and radionuclide signals representative of detected radionuclide emission signals, said data acquisition means including pulse counting circuitry operable at low count rates and high energy resolution for radionuclide emission detection, pulse counting circuitry operable at high count rates and moderate energy resolution for simultaneous radionuclide emission and transmission detection, and current mode circuitry operable at very high count rates without energy resolution for transmission detection,
   e) computer means for receiving and processing said transmission signals and developing an attenuation map for photons, said computer means receiving and processing said radionuclide signals using said attenuation map for attenuation correction and producing image signals of distribution of a radionuclide in an object positioned between said radiation source and said detector means, and
   f) display means responsive to said image signals.

2. The emission-transmission imaging system as defined by claim 1 wherein said computer means processes said transmission signals by reconstructing an image of at least one slice through an object using computed tomography (CT) attenuation coefficients developed from said photon signals.

3. The emission-transmission imaging system as defined by claim 2 wherein said computer means processes said radionuclide signals using said attenuation map to correct for at least one of photon attenuation, scattered radiation, and partial volume effects.

4. The emission-transmission imaging system as defined by claim 3 wherein said computer means receives and processes transmission signals from said detector means representative of a detected photon spectrum passed through a phantom for providing calibration data used in developing said attenuation map.

5. The emission-transmission imaging system as defined by claim 4 wherein said computer means iteratively processes said transmission signals and said radionuclide signals to reconstruct image signals of radionuclide distribution.

6. The emission-transmission imaging system as defined by claim 5 wherein said computer means uses subsets of complete radionuclide signals to reconstruct image subsets of radionuclide distribution which are combined to produce said image signals.

7. The emission-transmission imaging system as defined by claim 6 wherein said computer means reconstructs said image subsets concurrently with the acquisition of said radionuclide signals.

8. The emission-transmission imaging system as defined by claim 7 wherein said data acquisition means includes means for switching said pulse counting circuitry.

9. The emission-transmission imaging system as defined by claim 1 wherein said data acquisition means includes means for switching said pulse counting circuitry.

10. The emission-transmission imaging system as defined by claim 1 wherein said computer means iteratively processes said transmission signals and said radionuclide signals to reconstruct image signals of radionuclide distribution.

11. The emission-transmission imaging system as defined by claim 10 wherein said computer means uses subsets of complete radionuclide signals to reconstruct image subsets of radionuclide distribution which are combined to produce said image signals.

12. The emission-transmission imaging system as defined by claim 11 wherein said computer means reconstructs said image subsets concurrently with the acquisition of said radionuclide signals.

13. The emission-transmission imaging system as defined by claim 1 wherein said detector means comprises a single detector for photons.

14. The emission-transmission imaging system as defined by claim 1 wherein said detector means includes a first detector for photons from said radiation source and a second detector for photons from said radionuclide.

15. An emission-transmission imaging system comprising:
 a) an x-ray source for emitting an x-ray photon spectrum,
 b) an x-ray detector operated in the current-mode for detecting x-ray photons from the x-ray source,
 c) a radionuclide detector operated in the pulse-counting more for detecting photons corresponding to radionuclide emission,
 d) means for positioning the x-ray source facing the x-ray detector with an object containing a radionuclide between the x-ray source and the x-ray detector,
 e) means for maintaining relative positions of the x-ray detector and the radionuclide detector,
 f) an x-ray data acquisition system connected with the x-ray detector for receiving transmission signals from the x-ray detector,
 g) a radionuclide data acquisition system connected with the radionuclide detector for receiving emission signals from the radionuclide detector, representative of the radionuclide emission from the object,
 h) means for producing signals to maintain relative positions of x-ray and radionuclide data,
 i) computer means for receiving and processing the transmission signals and developing an attenuation map, and receiving and processing the radionuclide signals and producing image signals of distribution of a radionuclide of the object positioned between the x-ray source and the x-ray detector and radionuclide detector,
 j) a display system responsive to the image signals, and
 k) means for maintaining relative positions of said object with said x-ray detector and said radionuclide detector.

16. The emission-transmission imaging system as defined by 15 wherein the radionuclide data acquisition system has multiple energy windows and counters to receive and process the radionuclide detector signals.

17. The emission-transmission imaging system as defined in 15 wherein the radionuclide detector is scintillation camera.

18. The emission-transmission imaging system as defined in 15 wherein the x-ray detector includes a material selected from the group consisting of at least one of cadmium tungstate, cesium iodide, bismuth germanate, gadolinium oxysulfide, germanium, cadmium telluride, zinc cadmium telluride, lead iodide, mercuric iodide, and sodium iodide.

19. The emission-transmission imaging system as defined in 15 wherein a shaped filter is placed between the x-ray source and the object while the object is scanned to compensate for differences in x-ray absorption across the object.

20. The emission-transmission imaging system as defined by claim 15 wherein said computer means processes said transmission signals by reconstructing an image of at least one slice through an object using computed tomography (CT) attenuation coefficients developed from said transmission signals.

21. The emission-transmission imaging system as defined by claim 20 wherein said computer means processes said radionuclide signals using said attenuation map to correct for at least one of photon attenuation, scattered radiation, and partial volume effects.

22. The emission-transmission imaging system as defined by claim 21 wherein said computer means iteratively processes said transmission signals and said radionuclide signals to reconstruct image signals of radionuclide distribution.

23. The emission-transmission imaging system as defined by claim 22 wherein said computer means reconstructs image subsets concurrently with acquisition of said radionuclide signals.

24. An emission-transmission imaging system comprising
 a) a radiation source for emitting a photon spectrum,
 b) detector means for selectively detecting photons corresponding to said photon spectrum and photons corresponding to radionuclide emission, c) means for positioning said radiation source facing said detector means with an object positionable therebetween, said object having a radionuclide distribution therein, d) data acquisition means connected with said detector means for receiving signals from said detector means representative of the detected photon spectrum photons and radionuclide signals representative of detected radionuclide emission signals, e) computer means for receiving photon spectrum signals and for receiving said radionuclide signals, f) first processing means for developing an attenuation map from said photon spectrum signals, g) second processing means for constructing objective functions from subsets of said radionuclide signals, h) algorithm means for iteratively seeking an extremum of said objective functions to calculate image estimates of said radionuclide distribution contained in said object, and i) means for altering said subsets of said radionuclide signals and said objective functions to incorporate subsequently measured signals.

25. The system as defined by claim 24 wherein said computer means processes acquired subsets of radionuclides signals concurrently with acquisition of additional subsets of radionuclide signals.

26. The system as defined in claim 25 wherein said objective functions incorporates a physical characteristic selected from one of the following physical characteristics:

i) an approximation of the spatial response function of said emission-transmission imaging system, ii) an approximation of the photon attenuation properties of said object from said attenuation map, and iii) an approximation of the photon scattering properties of said object.

27. The system as defined by claim 26 wherein said objective functions include regularization terms that express prior knowledge of plausible attributes of said image estimates that cannot be inferred from projection measurements and said physical characteristics of the emission-transmission imaging system or said object.

28. The system as defined in claim 24 wherein said objective functions include at least one of maximum-likelihood or weighted least-squares functions.

29. The system as defined in claim 24 wherein said processing means for constructing said objective functions is started with a uniform image estimate and said subsets of radionuclide signals.

30. The system as defined in claim 29 wherein said processing means updates said objective functions and said image estimates incorporating additional subsets of radionuclide signals with existing subsets of radionuclide signals in subsequent iterative processes.

31. The system as defined in claim 30 wherein said iterative processes are continued until they include all said subsets of radionuclide signals.

32. The system as defined in claim 24 wherein said processing means for constructing objective functions uses a uniform image estimate and a single subset of radionuclide signals.

33. The system as defined in claim 32 wherein said processing means is repeated for each of said subsets of radionuclide signals.

34. The system as defined in claim 33 wherein said images estimates formed from said subsets of radionuclide signals are combined as a weighted linear combination of pixels from said image estimates.

35. The system as defined in claim 34 wherein said weighted linear combination is formed by multiplying said image estimates by the probability that said radionuclide photons are detected in said subset of radionuclide signals.

36. The system as defined in claim 35 wherein said objective functions include a physical characteristic selected from the following group of physical characteristics of said emission imaging system and said object:

i) an approximation of the spatial response function of said emission imaging system, ii) an approximation of the photon attenuation properties of said object, and iii) an approximation of the photon scattering properties of said object.

37. The system as defined in claim 36 wherein iterative reconstruction algorithms are applied to the image estimates calculated from said subsets of radionuclide signals.

* * * * *